United States Patent [19]

Nakatsukasa et al.

[11] 4,204,039

[45] May 20, 1980

[54] PROCESS FOR PRODUCING DEOXYNARASIN ANTIBIOTICS

[75] Inventors: Walter M. Nakatsukasa; Gary G. Marconi; Norbert Neuss, all of Indianapolis; Robert L. Hamill, Greenwood, all of Ind.

[73] Assignee: Eli Lilly and Company, Indianapolis, Ind.

[21] Appl. No.: 917,036

[22] Filed: Jun. 19, 1978

Related U.S. Application Data

[62] Division of Ser. No. 844,087, Oct. 20, 1977, Pat. No. 4,141,907.

[51] Int. Cl.$^2$ .................... C12P 17/16; C12R 1/485
[52] U.S. Cl. .................................... 435/118; 435/889
[58] Field of Search ........................................ 195/80 R

[56] References Cited

U.S. PATENT DOCUMENTS 4,038,384  7/1977  Berg et al. .......................... 195/80 R Primary Examiner—Alvin E. Tanenholtz
Attorney, Agent, or Firm—Nancy J. Harrison; Arthur R. Whale

[57] ABSTRACT

Deoxynarasin antibiotic complex, comprising 20-deoxynarasin and 20-deoxy-epi-17-narasin, is produced by submerged aerobic fermentation of *Streptomyces aureofaciens* NRRL 11181. 20-Deoxynarasin and 20-deoxy-epi-17-narasin are separated and isolated by chromatography. The deoxynarasin complex, 20-deoxynarasin and 20-deoxy-epi-17-narasin are antibacterial and anticoccidial agents and also increase feed-utilization efficiency in ruminants.

5 Claims, No Drawings

PROCESS FOR PRODUCING DEOXYNARASIN ANTIBIOTICS

This is a division of application Ser. No. 844,087, filed Oct. 20, 1977, and now U.S. Pat. No. 4,141,907.

BACKGROUND OF THE INVENTION

New improved antibiotics continue to be needed in veterinary medicine. For example, coccidiosis continues to be a wide-spread problem in the poultry industry. Coccidiosis results from infection by one or more species of *Eimeria* or *Isosproa* (for a summary see Lund and Farr in "Diseases of Poultry," 5th ed, Biester and Schwarte, Eds., Iowa State University Press, Ames, Iowa, 1965, pp. 1056-1096). Economic losses due to coccidiosis are great, creating a demand for better anticoccidial agents.

Promotion of growth in ruminants, such as cattle and sheep, is another economically desirable objective of veterinary science. Of particular interest is growth promotion achieved by increasing feed-utilization efficiency. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp. 408-410.

The relative efficiency of VFA utilization is discussed by McCullough in *Feedstuffs*, June 19, 1971, page 19; Eskeland et al. in *J. An. Sci.* 33, 282 (1971); and Church et al. in "Digestive Physiology and Nutrition of Ruminants," Vol. 2, 1971 pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate-utilization efficiency and also reducing the incidence of ketosis.

THE PRIOR ART

20-Deoxynarasin and 20-deoxy-epi-17-narasin are new polyether antibiotics; they are most closely related to the prior art polyether antibiotic narasin (antibiotic A-28086 factor A; U.S. Pat. Nos. 4,035,481 and 4,038,384). The structure of narasin proposed in these patents and by Occolowitz et al. [*Biomed. Mass Spectrometry* 3, 272-277 (1976)] was recently confirmed by H. Seto et al. [*J. Antibiotics* 30 (6) 530-532 (1977)] to be as shown in Formula 1:

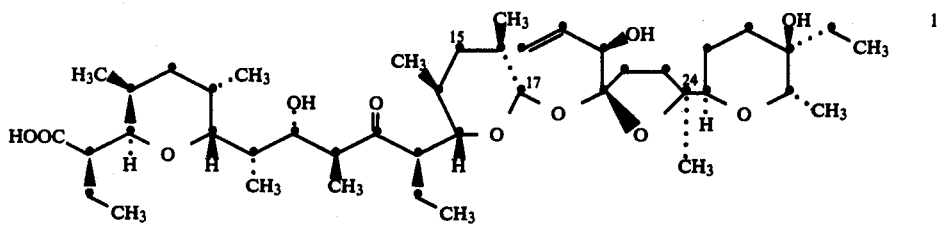

As Seto et al. report, narasin is closely related to salinomycin (salinomycin=4-demethylnarasin). More recently, J. W. Westley et al. reported on the C-17 epimers of deoxy-(O-8)-salinomycin [*J. Antibiotics* 30 (7) 610-612 (1977)]. Although the epimers of deoxysalinomycin are analogous to the epimers of deoxynarasin of this invention, there is no known chemical procedure by which the deoxynarasin epimers could be prepared from the deoxysalinomycin epimers.

SUMMARY OF THE INVENTION

This invention relates to antibiotic substances. In particular, it relates to the deoxynarasin antibiotic complex comprising at least two individual factors, 20-deoxynarasin and 20-deoxy-epi-17-narasin. The complex is produced by culturing a strain of the organism *Streptomyces aureofaciens* Duggar, NRRL 11181.

The term "antibiotic complex" as used in the fermentation art and in this specification does not refer to a chemical complex, but to a mixture of co-produced individual antibiotic factors. As will be recognized by those familiar with antibiotic production by fermentation, the ratio of individual factors produced in an antibiotic complex will vary, depending on the fermentation conditions used.

The pharmaceutically-acceptable salts of 20-deoxynarasin and 20-deoxy-epi-17-narasin are also part of this invention. To simplify discussions of utility, the term "deoxynarasin antibiotic" is used and refers to a member selected from the group consisting of deoxynarasin antibiotic complex, 20-deoxynarasin, 20-deoxy-epi-17-narasin, and the pharmaceutically-acceptable salts of 20-deoxynarasin and 20-deoxy-epi-17-narasin.

The deoxynarasin antibiotics of this invention inhibit the growth of organisms which are pathogenic to animal and plant life. In one aspect of this activity, the deoxynarasin antibiotics are anti-coccidial agents. In addition, the deoxynarasin antibiotics increase feed-utilization efficiency in ruminants.

DETAILED DESCRIPTION OF THE INVENTION

The deoxynarasin antibiotic complex comprises 20-deoxynarasin and 20-deoxy-epi-17-narasin which are obtained from the fermentation as a mixture. 20-Deoxynarasin and 20-deoxy-epi-17-narasin are separated from the deoxynarasin complex and isolated as individual compounds as hereinafter described. The deoxynarasin complex also contains minor factors which are removed by the procedures described. The deoxynarasin antibiotic complex is soluble in most organic solvents, but is insoluble in water.

20-DEOXYNARASIN

20-Deoxynarasin, one of the factors of this invention, has the same absolute configuration as narasin. The structure of 20-deoxynarasin is shown in Formula 2:

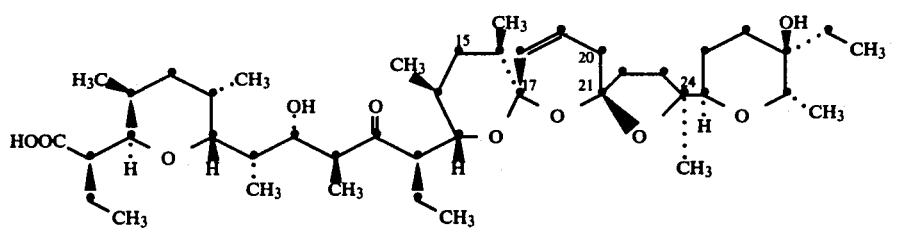

20-DEOXY-EPI-17-NARASIN

The structure of 20-deoxy-epi-17-narasin, the other factor of this invention, is shown in Formula 3.

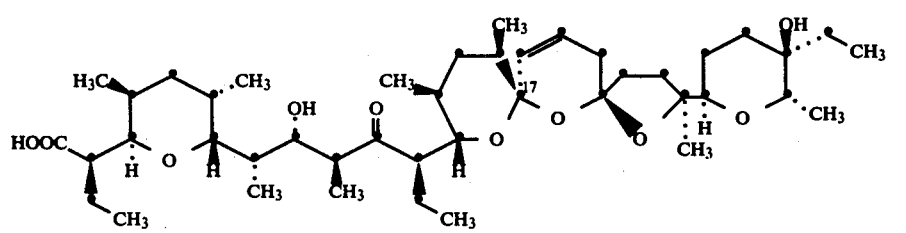

One of the best methods for differentiating narasin A-28086 factor A), 20-deoxynarasin, and 20-deoxy-epi-17-narasin is by the use of $^{13}C$ nuclear magnetic resonance (nmr) spectrometry. Table I summarizes the $^{13}C$ nmr spectra of these compounds, each as the free acid, run in deuterochloroform (data in ppm).

TABLE I

| Narasin | 20-Deoxynarasin | 20-Deoxy-epi-17-narasin |
|---------|-----------------|-------------------------|
| 216.5   | 216.8           | 218.0                   |
| 178.4   | 177.9           | 177.6                   |
| 132.0   | 125.2           | 129.2                   |
| 122.0   | 121.9           | 125.8                   |
| 106.5   | 105.0           | 107.0                   |
| 99.6    | 99.3            | 99.4                    |
| 88.5    | 88.1            | 85.6                    |
| 78.4    | 78.1            | 78.2                    |
| 77.1    | 76.6            | 77.7                    |
| 75.1    | 75.0            | 77.0                    |
| 73.8    | 73.7            | 73.3                    |
| 72.0    | 72.3            | 72.6                    |
| 70.8    | 71.1            | 71.1                    |
| 68.5    | 68.3            | 69.1                    |
| 67.6    | 56.2            | 57.7                    |
| 56.1    | 49.9            | 49.3                    |
| 49.9    | 49.3            | 48.7                    |

TABLE I-continued

| Narasin | 20-Deoxynarasin | 20-Deoxy-epi-17-narasin |
|---------|-----------------|-------------------------|
| 49.3    | 41.0            | 38.9                    |
| 41.1    | 40.0            | 36.6                    |
| 38.7    | 38.8            | 36.4                    |
| 36.6    | 36.3            | 36.2                    |
| 36.2    | 35.6            | 35.7                    |
| 35.5    | 32.8            | 33.9                    |
| 32.9    | 31.7            | 33.7                    |
| 30.9    | 31.7            | 32.8                    |
| 30.5    | 30.3            | 30.5                    |
| 29.4    | 29.6            | 29.3                    |
| 29.0    | 29.0            | 29.0                    |
| 28.0    | 28.1            | 28.2                    |
| 26.1    | 25.8            | 24.7                    |
| 24.0    | 23.7            | 23.3                    |
| 21.5    | 21.8            | 21.8                    |
| 19.0    | 18.8            | 21.1                    |
| 18.0    | 17.5            | 18.4                    |
| 16.4    | 16.3            | 18.2                    |
| 15.7    | 15.7            | 15.8                    |
| 14.3    | 14.1            | 14.3                    |
| 13.2    | 13.3            | 13.7                    |
| 13.0    | 13.2            | 13.5                    |
| 12.1    | 12.5            | 12.5                    |
| 12.1    | 12.1            | 12.1                    |
| 7.0     | 7.3             | 7.7                     |
| 6.3     | 6.5             | 6.4                     |

Other good methods for differentiating 20-deoxynarasin from 20-deoxy-epi-17-narasin and from the known A-28086 factors include paper and thin-layer chromatography. For example, the $R_f$ values of narasin (A-28086 factor A), A-28086 factor D, 20-deoxynarasin and 20-deoxy-epi-17-narasin in various paper-chromatographic systems, using *Bacillus subtilis* ATCC 6633 as a detection organism are given in Table II.

TABLE II

| Solvent System | Narasin | A-28086D | $R_f$ Values Deoxynarasin | Epideoxynarasin |
| --- | --- | --- | --- | --- |
| Water:methanol:acetone (12:3:1)-adjusted to pH 10.5 with NH$_4$OH and then lowered to pH 7.5 with H$_3$PO$_4$ | 0.20 | 0.11 | 0.08 | 0.21 |
| Water:methanol:acetone (12:3:1)-adjusted to pH 10.5 with NH$_4$OH and then lowered to pH 7.5 with HCl | 0.42 | 0.25 | 0.21 | 0.44 |
| 1% methyl isobutyl ketone (MIBK), 0.5% NH$_4$OH in water | 0.56 | 0.38 | 0.33 | 0.66 |
| Benzene saturated with water | 0.51 | 0.51 | 0.74 | 0.55 |
| Water:MIBK:ethyl acetate (98:1:1) | 0.77 | 0.61 | 0.51 | 0.68 |

The $R_f$ values of these antibiotics in a typical thin-layer chromatographic (TLC) system using silica gel are given in Table III.

TABLE III

| Solvent System | Narasin | A-28086D | $R_f$ Values Deoxynarasin | Epideoxynarasin |
| --- | --- | --- | --- | --- |
| Ethyl Acetate | 0.29 | 0.35 | 0.42 | 0.74 |

The deoxynarasin antibiotics (20-deoxynarasin and 20-deoxy-epi-17-narasin) are soluble in a variety of organic solvents such as, for example, methanol, ethanol, dimethylformamide, dimethyl sulfoxide, ethyl acetate, chloroform, acetone and benzene; but are only slightly soluble in nonpolar organic solvents such as hexane; and are insoluble in water. It should be noted, however, that 20-deoxynarasin free acid is unstable in alcohols, converting to 20-deoxy-epi-17-narasin free acid. For example, 20-deoxynarasin acid (435.1 mg) was dissolved in methanol (40 ml) and allowed to stand at room temperature for four hours. The solution was then evaporated to dryness under vacuum; the residue was redissolved in dioxane and lyophilized to give 417.8 mg of 20-deoxy-epi-17-narasin acid.

Another substance, chromatographically coincident with A-28086-I which is described in U.S. Pat. No. 4,038,384, is co-produced with the deoxynarasin complex. Although this substance initially co-precipitates with the deoxynarasin antibiotics, it is readily separated from them by silica-gel chromatography. On silica-gel thin-layer chromatography this substance is less polar than either 20-deoxynarasin or 20-deoxy-epi-17-narasin when ethyl acetate is the developing solvent. Vanillin spray reagent (3% vanillin in methanl+0.5 ml conc H$_2$SO$_4$ per 100 ml of solution) is convenient for detection. After spraying with vanillin and heating, this substance, like A-28086-I, gives a blue spot while the deoxynarasin antibiotics give bright yellow spots which darken later.

20-Deoxynarasin and 20-deoxy-epi-17-narasin are capable of forming salts. The pharmaceutically-acceptable alkali-metal, alkaline-earth-metal and amine salts of 20-deoxynarasin and 20-deoxy-epi-17-narasin are also part of this invention. "Pharmaceutically acceptable" salts are salts in which the toxicity of the compound as a whole toward warm-blooded animals is not increased relative to the non-salt form. Representative and suitable alkali-metal and alkaline-earth-metal salts of 20-deoxynarasin and 20-deoxy-epi-17-narasin include the sodium, potassium, lithium, cesium, rubidium, barium, calcium, and magnesium salts. Suitable amine salts of 20-deoxynarasin and 20-deoxy-epi-17-narasin include the ammonium and the primary, secondary and tertiary $C_1$–$C_4$-alkylammonium and hydroxy-$C_2$–$C_4$-alkylammonium salts. Illustrative amine salts include those formed by reaction of 20-deoxynarasin and 20-deoxy-epi-17-narasin with ammonium hydroxide, methylamine, sec-butylamine, isopropylamine, diethylamine, diisopropylamine, ethanolamine, triethylamine, 3-amino-1-propanol and the like.

The alkali-metal and alkaline-earth-metal cationic salts of 20-deoxynarasin and 20-deoxy-epi-17-narasin are prepared according to procedures commonly employed for the preparation of cationic salts. For example, the free acid form of the antibiotic is dissolved in a suitable solvent such as acetone or dioxane-water; a solution containing the stoichiometric quantity of the desired inorganic base is added to this solution. The salt thus formed can be isolated by routine methods, such as filtration or evaporation of the solvent.

The salts formed with organic amines can be prepared in a similar manner. For example, the gaseous or liquid amine can be added to a solution of the antibiotic factor in a suitable solution such as acetone, and the solvent and excess amine can be removed by evaporation.

A preferred method for the preparation of a desired salt of one of the deoxynarasin antibiotics is an appropriate initial choice of isolation procedure, such as, for example, adjusting the pH of the broth with an appropriate base or adding an appropriate cationic salt to the extracting solvent.

It is well known in the veterinary pharmaceutical art that the form of an antibiotic is not significant when treating an animal with the antibiotic. In most cases, conditions within the animal change the drug to forms other than the form in which it was administered. The salt form in which it may be administered is, therefore, insignificant to the method of treatment. The salt form may, however, be chosen for reasons of economics, convenience, and toxicity.

The novel antibiotics of this invention are produced by culturing a deoxynarasin-producing strain of *Streptomyces aureofaciens* under submerged aerobic conditions in a suitable culture medium until substantial antibiotic activity is produced. The antibiotics are recovered by using various isolation and purification procedures commonly used and understood in the art.

The organism useful for the preparation of the deoxynarasin antibiotics was obtained by N-methyl-N'-nitro-N-nitrosoguanidine-induced mutation of *Streptomyces aureofaciens* NRRL 8092. The basis on which *S. aureofaciens* NRRL 8092 was classified as a strain of

*Streptomyces aureofaciens* Duggar, is described in U.S. Pat. No. 4,038,384.

The *Streptomyces aureofaciens* culture useful for production of the deoxynarasin antibiotics has been deposited and made a part of the stock culture collection of the Northern Regional Research Center, U.S. Dept. of Agriculture, Agricultural Research Service, Peoria, Ill., 61604, from which it is available to the public under the number NRRL 11181.

It will be recognized by those skilled in the art that, given our invention, it should now be possible to generate additional strains which have essentially the same biosynthetic capabilities as *S. aureofaciens* NRRL 11181 (i.e., the ability to produce 20-deoxynarasin and 20-deoxy-epi-17-narasin) by subjecting *S. aureofaciens* NRRL 5758, NRRL 8092, or NRRL 11181, to mutagenic treatment. Although N-methyl-N'-nitro-N-nitrosoguanidine was used to obtain *S. aureofaciens* NRRL 11181, other known mutagens such as ultraviolet rays, X-rays, high-frequency waves, radioactive rays and other chemical agents could be used to induce a similar mutagenesis. Part of our invention, therefore, is the method of producing deoxynarasin antibiotic complex which comprises cultivating a *Streptomyces aureofaciens* having essentially the same biosynthetic capabilities of NRRL 11181.

The culture medium used to grow *Streptomyces aureofaciens* NRRL 11181 can be any one of a number of media. For economy in production, optimal yield, and ease of product isolation, however, certain culture media are preferred. Thus, for example, preferred carbohydrate sources in large-scale fermentation are tapioca dextrin and sucrose, although glucose, corn starch, fructose, mannose, maltose, lactose, and the like can also be employed. Corn oil, peanut oil, soybean oil and fish oil are other useful sources of carbon. A preferred nitrogen source is enzyme-hydrolyzed casein, although peptones, soybean meal, cottonseed meal, amino acids such as glutamic acid, and the like are also useful. Among the nutrient inorganic salts which can be incorporated in the culture media are the customary soluble salts capable of yielding sodium, magnesium, calcium, ammonium, chloride, carbonate, sulfate, nitrate, and like ions.

Essential trace elements necessary for the growth and development of the organism should also be included in the culture medium. These trace elements commonly occur as impurities in other constituents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

Although it is not essential, antibiotic production is enhanced by the addition of a small amount of oil such as soybean oil.

For production of substantial quantities of the deoxynarasin antibiotics, submerged aerobic fermentation in tanks is preferred. Smaller quantities may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that employed for larger fermentations, but other media can also be employed.

The deoxynarasin-producing organism can be grown at temperatures between about 20° and about 40° C. Optimum deoxynarasin production appears to occur at temperatures of about 27°-30° C.

As is customary in aerobic submerged culture processes, sterile air is blown through the culture medium. For efficient growth of the organism the volume of air used in tank production is preferably above 0.1 volume of air per volume of culture medium per minute. For efficient antibiotic production the volume of air used in tank production is preferably above 0.25 volume of air per volume of culture medium per minute. High levels of dissolved oxygen do not depress antibiotic production.

Production of the antibiotics can be followed during the fermentation by testing samples of the broth or of extracts of the mycelial solids for antibiotic activity against organisms known to be sensitive to the antibiotics. One assay organism useful in testing the antibiotics of the present invention is *Bacillus subtilis* ATCC 6633. The bioassay is conveniently performed by paper-disc assay on agar plates.

Another convenient monitoring method is by turbidometric assay on a semiautomated system (Autoturb ® microbiological assay system, Elanco) described by N. R. Kuzel and F. W. Kavanaugh in *J. Pharmaceut. Sci.* 60 (5), 764 and 767 (1971). In testing the deoxynarasin antibiotics, the following test parameters are used: *Staphylococcus aureus* (H-Heatley) NRRL B-314 in a nutrient broth medium (pH 7), incubated for four hours at 37° C. Test samples and standard are dissolved in methanol-water (1:1). The standard, A-28086 factor A, is presented to the Autoturb ® carrousel at concentrations of 1, 2, 3, 4, and 5 mcg/ml.

The initial pH of the uninoculated culture medium varies with the medium used. In general, the pH should be in the range of 6.0 to 7.5. The harvest pH at the end of the fermentation is usually slightly higher, in the range of 6.5 to 8.0.

Generally, antibiotic activity is detectable as early as the second day of the fermentation. Maximum production of antibiotic activity usually occurs between about the fourth and the tenth days.

Following their production under submerged aerobic fermentation conditions, the deoxynarasin antibiotics previously described can be recovered from the fermentation medium by methods commonly used in the fermentation art. The antibiotics produced during the fermentation occur in both the mycelial mass and in the filtered broth. Maximum recovery of the deoxynarasin antibiotics is accomplished, therefore, by a combination of methods, including filtration, extraction, and adsorption chromatography. A preferred solvent for separating the deoxynarasin antibiotics from either whole or filtered fermentation broth is ethyl acetate, although other commonly used solvents are satisfactory.

An especially advantageous method of separating the deoxynarasin antibiotics is to lower the pH of the whole fermentation broth to about pH 3.0. At this pH the deoxynarasin antibiotics are conveniently separated with the mycelial mass by filtration. This method is described for recovery of the related antibiotics, A-28086 factors A, B, and D and salinomycin, by Boeck and Berg in U.S. Pat. No. 4,009,262. Another advantageous aspect of this method involves adding a bicarbonate such as, for example, sodium bicarbonate, to the whole broth in amounts of approximately one gram per liter. Using this method, the deoxynarasin antibiotics are conveniently separated with the mycelial mass in salt form. Methanol is a preferred solvent for separating the antibiotics from the mycelial mass, but other lower alcohols and ketones are also suitable.

Azeotropic distillation can also be advantageously used in recovery of the deoxynarasin antibiotics. In this method an organic solvent which forms an appropriate azeotrope with water is added to the aqueous fermentation broth. This solvent-broth mixture is subjected to azeotropic distillation in order to remove at least half the water from the broth, leaving a water-solvent mixture in which the deoxynarasin antibiotics are in solution in the organic solvent. Insoluble by-products can be separated by suitable means such as filtration or centrifugation. The deoxynarasin antibiotics can then be recovered from the organic solution by well-known procedures such as evaporation of solvent, precipitation by adding a nonsolvent, or extraction.

Organic solvents which form appropriate azeotropes with water in order to carry out such a recovery procedure include, illustratively, butyl alcohol, amyl alcohol, hexyl alcohol, benzyl alcohol, butyl acetate, amyl acetate, 1,2-dichloroethane, 3-pentanone, 2-hexanone, benzene, cyclohexanone, toluene, the xylenes and the like.

There is special advantage in recovery by azeotropic distillation on large-scale fermentation processes. Both water and solvent taken overhead in the azeotrope can be separated by known techniques and thereafter recycled for further use. The water thus removed is free of contaminants and does not require a waste disposal process.

Further purification of the deoxynarasin antibiotics includes additional extraction and adsorption procedures. Adsorptive materials such as silica gel, carbon, Florisil ® (magnesium silicate, Floridin Co., P.O. Box 989, Tallahassee, Fla.) and the like can be advantageously used.

Alternatively, the culture solids, including medium constituents and mycelium can be used without extraction or separation, but preferably after removal of water, as a source of the deoxynarasin antibiotic complex. For example, after production of deoxynarasin antibiotic activity, the culture medium can be dried by lyophilizing or drum drying and mixed directly into feed premix.

In another aspect, after production of deoxynarasin activity in the culture medium, the mycelium can be separated and dried to give a product which can be used directly in a feed premix. When separating the mycelium for such use, the addition of calcium carbonate (about 10 g/l.) aids in filtration and gives an improved dried product.

Under the conditions used thus far, 20-deoxynarasin and 20-deoxy-epi-17-narasin are recovered as the major factors from the *Streptomyces aureofaciens* strain described previously and designated as NRRL 11181. Some minor factors are also recovered from *S. aureofaciens* NRRL 11181 in amounts too small to permit characterization. Although the ratio of factors varies depending on the fermentation and isolation conditions used, in general more 20-deoxy-epi-17-narasin is recovered than 20-deoxynarasin is recovered.

20-Deoxynarasin and 20-deoxy-epi-17-narasin are separated from each other and isolated as individual compounds by the use of well-known methods such as column chromatography, thin-layer chromatography, counter-current distribution and the like. For example, column chromatography over silica gel is used to separate 20-deoxynarasin and 20-deoxy-epi-17-narasin by eluting the column with varying solvent mixtures. For example, using benzene-ethyl acetate solvent mixtures over a silica-gel column, 20-deoxy-epi-17-narasin is eluted first, and 20-deoxynarasin is eluted later. Thin-layer chromatography on silica gel, using a 100% ethyl acetate solvent, is a convenient method for monitoring elution progress.

The deoxynarasin antibiotics of this invention are antibacterial agents. For example, the relative microbiological activity of 20-deoxy-epi-17-narasin (free acid) is described in Table IV. The conventional disc-diffusion method was used.

TABLE IV

| Test Organism | | Zone of Inhibition (mm) | |
|---|---|---|---|
| | | 300 mcg/disc | 30 mcg/disc |
| Staphylococcus aureus | 3055 | 16.9 | 13.8 |
| Staphylococcus aureus | 3074[1] | 19.5 | 15.4 |
| Staphylococcus aureus | 3130[2] | 19.0 | 17.2 |
| Streptococcus pyogenes | (Group A) | 12.0 | 10.0 |
| Streptococcus sp. | (Group D) | 17.0 | 14.6 |
| Dipplococcus pneumoniae | | 16.0 | 13.0 |

[1]Penicillin G Resistant
[2]Methicillin Resistant

In one aspect, the deoxynarasin antibiotics inhibit the growth of anaerobic bacteria. The minimal inhibitory concentrations (MIC) at which 20-deoxy-epi-17-narasin (free acid) inhibits various anaerobic bacteria, determined by standard agar-dilution assay, are summarized in Table V. End points were read after 24-hour incubation period.

TABLE V

| ANAEROBIC BACTERIA | MIC (mcg/ml) |
|---|---|
| *Actinomyces israelii* W855 | 8 |
| *Clostridium perfringens* 81 | 16 |
| *Clostridium septicum* 1128 | 16 |
| *Eubacterium aerofaciens* 1235 | 16 |
| *Peptococcus asaccharolyticus* 302 | 8 |
| *Peptococcus prewoti* 1281 | 4 |
| *Peptostreptococcus anaerobius* 1428 | 4 |
| *Peptostreptococcus intermedius* 1264 | 4 |
| *Propionibacterium acnes* 79 | 2 |
| *Bacteroides fragilis* 111 | >128 |

Activity against Mycoplasma is another useful aspect of the antimicrobial activity of the deoxynarasin antibiotics. Mycoplasma species, also known as pleuropneumonia-like (PPLO) organisms, are pathogenic to man and various animals. Agents active against PPLO organisms are especially needed by the poultry industry. The minimal inhibitory concentrations (MIC) of 20-deoxy-epi-17-narasin (free acid) against illustrative Mycoplasma species, as determined by in vitro broth-dilution studies, are summarized in Table VI.

| Organism | MIC(mcg/ml) |
|---|---|
| M. gallisepticum | 0 |
| M. hyorhinis | 50.0 |
| M. synoviae | 50.0 |

The deoxynarasin antibiotics are also antiviral agents. For example, 20-deoxy-epi-17-narasin is active against rhinovirus type 3, vaccinia virus, herpesvirus and influenza A virus, as demonstrated by in vitro plaque suppression tests, similar to that described by Siminoff, *Applied Microbiology* 9 [1], 66–72 (1961).

In one aspect of this invention, therefore, a deoxynarasin antibiotic can be administered orally, topically or parenterally to mammals for the control of viruses. Useful dosage levels for prevention or treatment of viral disease vary from about 1 to about 5 mg/kg of mammalian body weight, depending upon the virus and upon whether the drug is to be used prophylactically or therapeutically.

Furthermore, solutions containing a deoxynarasin antibiotic, preferably together with a surfactant, can be used to decontaminate the in vitro habitat on which viruses, such as polio or herpes, are present. Solutions containing from about 1 to about 1500 mcg/ml of a deoxynarasin antibiotic are effective in the control of viruses.

The acute toxicities of 20-deoxy-epi-17-narasin (free acid) and 20-deoxynarasin (Na salt), when administered intraperitoneally to mice and expressed as $LD_{50}$, are 201 mg/kg and 5 mg/kg, respectively.

Anticoccidial activity is an important property of the deoxynarasin antibiotics of this invention. For example, in vitro experiments show that 20-deoxynarasin (Na salt) and 20-deoxy-epi-17-narasin (free acid) are active against *Eimeria tenella*, the protozoan organism most associated with coccidiosis, at levels as low as 0.2 ppm.

A feeding experiment in young chickens confirms that the deoxynarasin antibiotics have anticoccidial activity in vivo. In this experiment 20-deoxynarasin (Na salt), administered at a level of 100 ppm in the diet to chicks challenged with *Eimeria tenella*, prevented mortality, improved weight gains, and decreased the number of lesions in the chicks. The results of this experiment are summarized in Table VII.

TABLE VII

| Treatment[1] | % Mortality | Weight Gain (g) | Lesion Score[2] |
|---|---|---|---|
| Infected Controls | 37.5 | 114 | 4.00 |
| 20-Deoxynarasin (100 ppm) | 0 | 185 | 0.13 |

[1]Two cages of four chickens each per treatment.
[2]Maximum possible score = 4.00.

For the prevention or treatment of coccidiosis in poultry, an effective anticoccidial amount of deoxynarasin antibiotic is administered to birds, preferably orally on a daily basis. The deoxynarasin antibiotic can be supplied in many ways, but it is most conveniently supplied with a physiologically-acceptable carrier, preferably the feed ingested by the birds. Although a variety of factors must be considered in determining an appropriate concentration of deoxynarasin antibiotic, the rates of administration will be generally in the range of 0.003 to 0.03 percent by weight of unmedicated feed, and preferably in the range of 0.004 to 0.02 percent.

This invention also relates to anticoccidial feed compositions for poultry comprising poultry feed and from about 35 to about 180 grams per ton of a deoxynarasin antibiotic.

The ability to improve feed-utilization efficiency in animals is another important property of the deoxynarasin antibiotics. For example, deoxynarasin antibiotics improve feed-utilization efficiency in ruminants which have a developed rumen function.

As discussed, efficiency of carbohydrate utilization in ruminants is increased by treatments which stimulate the animal's rumen flora to produce propionate compounds rather than acetate or butyrate compounds. The efficiency of feed use can be monitored by observing the production and concentration of propionate compounds in rumen fluid, using methods as described in U.S. Pat. No. 4,038,384.

Results of in vitro tests with 20-deoxynarasin (Na salt) and 20-deoxy-epi-17-narasin (free acid), showing the ratio of volatile-fatty-acid (VFA) concentrations in treated flasks to concentrations in control flasks, are shown in Table VIII.

TABLE VIII

| | | Ratio of Treated to Control | | | |
|---|---|---|---|---|---|
| Compound | Dose mcg/ml | Molar % acetate | Molar % propionate | Molar % butyrate | Total VFA |
| 20-deoxy-epi-17-narasin | 10 | 0.9093 | 1.2665* | 0.6560 | 1.0325 |
| " | 5 | 0.9237 | 1.1836* | 0.8201 | 1.0487 |
| " | 2 | 0.9581 | 1.0858 | 0.9414 | 1.0717 |
| 20-deoxynarasin | 1 | 0.8727 | 1.4597* | 0.3942 | 1.2096 |
| " | 0.3 | 0.9084 | 1.3799* | 0.4582 | 1.1829 |
| " | 0.1 | 0.9504 | 1.2148* | 0.6870 | 1.1892 |

*Statistically significant ($P<0.01$) by the two-tailed LSD test (R. G. D. Steel and J. H. Torrie, "Principles and Procedures of Statistics," McGraw-Hill, New York, N.Y., 1960, p. 106)

The deoxynarasin antibiotics of this invention are typically effective in increasing propionates and, thereby, the efficiency of feed-utilization when administered to ruminants orally at rates of from about 0.05 mg/kg/day to about 5.0 mg/kg/day. Most beneficial results are achieved at rates of from about 0.1 mg/kg/day to about 2.5 mg/kg/day. A preferred method of administration of an antibiotic of this invention is by mixing it with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of a compound of this invention directly related to the proper daily dose for the animal to be treated.

This invention further relates to feed compositions adapted to fatten ruminants such as cattle and sheep. These feed compositions comprise cattle feed and from 1 to 30 grams per ton of a deoxynarasin antibiotic.

Swine dysentery is a common disease in the United States and other countries, annually causing losses in stock to swine growers world-wide. U.S. Pat. No. 3,947,586 teaches that polyether antibiotics are useful in the prevention and treatment of swine dysentery. Since the deoxynarasin antibiotics are new members of the class of polyether antibiotics, they should also be effective in the prevention and treatment of swine dysentery.

For the prevention or treatment (control) of dysentery in swine, it is preferable to incorporate an effective amount of a deoxynarasin antibiotic into the feed ration.

The deoxynarasin antibiotics of this invention should be typically effective in preventing or controlling swine dysentery when administered to swine orally at rates of from about 35 to about 150 grams per ton of active compound. An especially preferred rate should be about 100 grams of active compound per ton. Although the preferred method of administration is by mixing it with the animals' feed, it can also be administered in other ways, for example, tablets, drenches, boluses, or capsules. Each individual dosage unit should contain a quantity of an antibiotic of this invention directly related to the proper daily dose for the animal to be treated.

This invention further relates to feed compositions for swine comprising swine ration and an effective amount of a deoxynarasin antibiotic. As discussed, an effective amount is typically one in the range of from about 35 to about 150 grams of a deoxynarasin antibiotic per ton of feed.

The deoxynarasin antibiotics are antiviral agents and are also active against anaerobic bacteria, such as *Clostridium perfringens*. The deoxynarasin antibiotics are, therefore, beneficial in the treatment or prevention of enteritis in chickens, swine, cattle and sheep and in the treatment of enterotoxemia in ruminants.

Certain deoxynarasin compounds (20-deoxynarasin and its salts) exhibit ion-binding and ion-transport properties and are, therefore, ionophores (ion-bearers) (see B. C. Pressman, Alkali Metal Chelators- The Ionophores, in "Inorganic Biochemistry," Volume 1, G. L. Eichhorn, Elsevier, 1973). These compounds can be used when the selective removal of a particular cation is desired. Examples of such uses include the removal and recovery of silver ions from solutions in photography, the removal of toxic cations from industrial waste streams before such streams are discharged to the environment, and desalinization of sea water. A deoxynarasin compound can be used as one component of an ion-specific electrode (see O. Kedem, et al., U.S. Pat. No. 3,753,887). These compounds are alter the cation permeability of both natural and artificial membranes. A deoxynarasin compound can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, Science 172, 377 (1971)].

In yet another aspect, 20-deoxynarasin and its salts are active as an inhibitor of the enzyme ATPase. ATPase, an alkali-metal-sensitive enzyme found in cell membranes, is involved in the energy necessary for active transport. "Active transport" refers to the energy-requiring series of operations whereby intracellular and extracellular fluids maintain their compositions. Inhibitors of ATPase reduce the energy required for active transport. In vitro tests have shown that 20-deoxynarasin (Na salt) inhibits cation transport ATPase in liver mitochondria at a half effective concentration of 0.065 mcg/ml.

20-Deoxynarasin and its salts are also potential cardiotonic agents. In tests using isolated guinea-pig atria, for example, 20-deoxynarasin increased cardiac contractility. Response to this test is expressed as a percentage of the maximal contractile tension that could be elicited by a challenge dose of norepinephrine $(10^{-4})$M). 20-Deoxynarasin (Na salt), at a $10^{-5}$ molar concentration, produced a mean ($\pm$ standard error) increase in contractile tension of $43.8\pm1.4$ (n=4) percent. For a more detailed description of this test, see U.S. Pat. No. 3,985,893.

Our invention includes, therefore, the method of enhancing the contractile force of mammalian heart muscle in a warm-blooded mammal which comprises administering an effective nontoxic dose of 20-deoxynarasin or a pharmaceutically acceptable salt thereof. An effective nontoxic dose is a dose in the range of from about 30 to about 500 mcg/kg of body weight. A preferable does range is below about 100 mcg/kg of body weight. For this method, the antibiotic is administered parenterally, for example by intravenous infusion. A suitable method of administration is the drip method wherein the antiobiotic is incorporated in a standard i.v. solution such as a dextrose solution.

20-Deoxynarasin is preferably administered at doses below about 100 mcg/kg until the desired enhancement of the contractile force is observed. Thereafter the amount of 20-deoxynarasin administered can be regulated by the rate of infusion needed to maintain the desired response. As with the clinical administration of other inotropic agents, the dose of 20-deoxynarasin administered may be varied in a given clinical case according to such factors as the individual's tolerance of 20-deoxynarasin, the nature of the heart's affliction, e.g., the extent of damage to the heart muscle, and the age and general physical condition of the patient.

The method of this invention comprising the use of the positive inotropic agent 20-deoxynarasin can be used in a variety of clinical situations broadly classified as cardiogenic shock. Such conditions include, for example, myocardial infarction, congestive heart failure, and post operative cardiogenic shock.

In order to illustrate more fully the operation of this invention the following examples are provided.

EXAMPLE 1

A. Shake-flask fermentation

A culture of *Streptomyces aureofaciens* NRRL 11181 was prepared and maintained on an agar slant having the following composition:

| Ingredient | Amount |
|---|---|
| $K_2HPO_4$ | 2 g |
| $MgSO_4 . 7H_2O$ | 0.25 g |
| $NH_4NO_3$ | 2 g |
| $CaCO_3$ | 2.5 g |
| $FeSO_4 . 7H_2O$ | 0.001 g |
| $MnCl_2 . 7H_2O$ | 0.001 g |
| $ZnSO_4 . 7H_2O$ | 0.001 g |
| Glucose | 10 g |
| Agar | 20 g |
| Deionized water | q.s. 1 liter |
| pH (unadjusted) | 7.7 |

The slant was inoculated with *Streptomyces aureofaciens* NRRL 11181, and the inoculated slant was incubated at 30° C. for up to 7 days. The mature slant culture was covered with sterile beef serum and scraped with a sterile loop to loosen the spores. The resulting beef-serum suspension of spores and mycelial fragments was lyophilized into a maximum of 6 pellets.

One lyophilized pellet thus prepared was used to inoculate 50 ml of a vegetative medium having the following composition:

| Ingredient | Amount |
| --- | --- |
| Glucose | 20 g |
| Soybean flour | 15 g |
| Corn-steep liquor | 10 g |
| CaCO₃ | 2 g |
| Tap water | q.s. 1 liter |
| pH adjusted to 6.5 by addition of 5 N NaOH | |

The inoculated vegetative medium, in a 250-ml Erlenmeyer flask, was incubated at 30° C. for some 24 to 48 hours on a shaker rotating through an arc 2 inches in diameter at 250 RPM.

The incubated vegetative medium above described (50 ml) was used to inoculate 250 ml of one of the following fermentation media:

| Medium I: | |
| --- | --- |
| Ingredient | Amount |
| Tapioca dextrin* | 60 g |
| Enzyme-hydrolyzed casein** | 6 g |
| Enzymatic hydrolysate of casein*** | 2 g |
| CaCO₃ | 2 g |
| MgSO₄ . 7H₂O | 0.5 g |
| Blackstrap molasses | 15 g |
| Refined soybean oil | 5.0 ml/L |
| Tap H₂O | q.s. 1 liter |
| pH (unadjusted) | 6.6 |

*Stadex 11, A. E. Staley, Decatur, Illinois
*Amber EHC, Amber Laboratories, Juneau, Wisc.
***N-Z Amine A, Sheffield Chemical Co., Norwich, New York

| Medium II: | |
| --- | --- |
| Ingredient | Amount |
| Tapioca dextrin* | 30 g |
| Glucose | 15 g |
| Enzyme hydrolyzed casein** | 3 g |
| Enzymatic hydrolysate of casein*** | 1 g |
| Yeast extract | 2.5 g |
| CaCO₃ | 2 g |
| MgSO₄ . 7H₂O | 1 g |
| Blackstrap molasses | 15 g |
| Refined soybean oil | 5.0 ml/L |
| Tap H₂O | q.s. 1 liter |
| pH (unadjusted) | 6.4 |

*Stadex 11, A. E. Staley, Decatur, Illinois
**Amber EHC, Amber Laboratories, Juneau, Wisc.
***N-Z Amine A, Sheffield Chemical Co., Norwich, New York

| Medium III: | |
| --- | --- |
| Ingredient | Amount |
| Soybean flour | 25 g |
| Glucose | 20 g |
| CaCO₃ | 2.0 g |
| Na₂SO₄ . 10H₂O | 1.0 g |
| Refined soybean oil | 20 ml |
| Methyl oleate | 20 ml |
| FeSO₄ . 7H₂O | 0.6 g |
| MnCl₂ . 4H₂O | 0.3 g |
| Ascorbic acid | 0.018 g |
| Deionized H₂O | q.s. 1 liter |
| pH (unadjusted) | 6.5 |

The fermentation was incubated for a period of up to 10 days at 30° C. on a 250-RPM rotary shaker with a 2-inch arc.

B. Tank Fermentation

The tank fermentation is carried out using vegetative and fermentation media as described in Section A for shake-flask fermentation. For tank fermentation 10 ml of the vegetative medium are used to inoculate 400 ml of a second-stage vegetative medium in an 2-liter Erlenmeyer flask. After a 24-hour incubation at 30° C., 800 ml of the second-stage vegetative medium are used to inoculate 100 liters of fermentation medium in a 165-liter fermentation tank. The pH of the medium after sterilization at 121° C. for 45 minutes is approximately 6.8±0.1. Fermentation is allowed to proceed for 10 days at 30°±1° C. The tank is aerated with sterile air at a rate of 0.5 volumes of air per volume of culture medium per minute, stirring with conventional agitators at 300 RPM.

EXAMPLE 2

Separation of the Deoxynarasin Complex

The pH of whole fermentation broth (4 l), obtained by the method described in Example 1 using medium II, was lowered to pH 3.0 by the addition of conc. HCl, stirring for 1 hour. The resulting solution was filtered with a filter aid (125 g Hyflo Super-Cel, a diatomaceous earth, Johns-Manville Corp.). The separated mycelial cake was extracted batchwise, using a blender, with a total of 2 liters of methanol which contained 50 g NaHCO₃ per liter. The methanol filtrate was evaporated under vacuum to a volume of approximately 450 ml; the pH of this solution was adjusted to pH 7.5 by the addition of conc. HCl. The resulting solution was extracted twice with CHCl₃ (500 ml). The CHCl₃ extracts were combined, dried over Na₂SO₄ and filtered. The filtrate was evaporated under vacuum to give 2.0 g of crude deoxynarasin complex.

EXAMPLE 3

Isolation of Deoxynarasin and Epi-Deoxynarasin

Crude deoxynarasin complex (2 g), obtained as described in Example 2, was dissolved in a minimal amount of benzene and applied to a 1.5-×22-cm column of silica gel (Merck 7729). The fractions isolated, solvents used, and amounts yielded are shown in the following table:

| Fraction | Volume | Solvent | Ratio | Yield (mg)* |
| --- | --- | --- | --- | --- |
| 1 | 3.0 l. | Benzene | 100% | 24 |
| 2 | 2.0 l. | Benzene:ethyl acetate | 9:1 | 20 |
| 3 | 600 ml | " | 4:1 | 85 |
| 4 | 300 ml | " | " | 5 |
| 5 | 300 ml | " | " | 7 |
| 6 | 900 ml | " | " | 18 |
| 7 | 2.0 l. | " | " | 22 |
| 8 | 300 ml | " | " | 7 |
| 9 | 450 ml | " | " | 22 |
| 10 | 450 ml | " | " | 9 |
| 11 | 1.2 l. | " | " | 7 |
| 12 | 1.2 l. | " | " | 5 |
| 13 | 1.0 l. | " | " | 12 |
| 14 | 1.0 l. | " | 3:1 | 14 |
| 15 | 1.5 l. | " | " | 28 |
| 16 | 1.5 l. | " | " | 100 |
| 17 | 450 ml | " | " | 26 |
| 18 | 900 ml | Benzene:ethyl acetate | 3:1 | 70 |
| 19 | 1.0 l. | " | " | 54 |
| 20 | 300 ml | Ethyl acetate | 100% | 12 |

-continued

| Fraction | Volume | Solvent | Ratio | Yield (mg)* |
|---|---|---|---|---|
| 21 | 150 ml | " | " | 180 |
| 22 | 150 ml | " | " | 125 |
| 23 | 450 ml | " | " | 170 |
| 24 | 300 ml | Methanol | " | 40 |
| 25 | 450 ml | " | " | 1100 |

*obtained after drying over $Na_2SO_4$, filtering and evaporating filtrate to dryness under vacuum.

Fractions were monitored by TLC, using an ethyl acetate solvent system. Fractions 16–17 (126 mg) contained 20-deoxy-epi-17-narasin. Fractions 18–23 contained a mixture of 20-deoxynarasin and 20-deoxy-epi-17-narasin.

A mixture of 20-deoxynarasin and 20-deoxy-epi-17-narasin, obtained as above-described for fractions 18–23, was chromatographed by preparative TLC, using an ethyl acetate solvent system. The mixture (105 mg on one plate and 130 mg on another plate) was dissolved in a small amount of $CH_2Cl_2$ and placed on a silica-gel (Merck) preparative plate. After the plate had been allowed to develop, the two separated materials were observed by ultraviolet light. Each of the areas representing the two materials were removed from the plate and extracted with $CH_2Cl_2$: $CH_3OH$ (4:1). In this system deoxynarasin is the slower moving of the two components. From the plate containing 105 mg material, 7.5 mg of 20-deoxy-epi-17-narasin and 27 mg of deoxynarasin were recovered. From the plate containing 130 mg of mixture, 4.0 mg of 20-deoxy-epi-17-narasin and 56 mg of 20-deoxynarasin were recovered.

EXAMPLE 4

Alternate Isolation of 20-Deoxynarasin

Whole fermentation broth (95 l) was adjusted to about pH 3 by the addition of HCl and then was stirred for 1 hour. Filter aid (Hyflo Supercel, 3%) was added, and the broth was filtered. The separated mycelial cake was extracted twice with about 45 l. of acetone which contained 50 g of $NaHCO_3$ per liter. The acetone extracts were combined and concentrated under vacuum to give about 10 liters of aqueous solution. The pH of this solution was adjusted to 8.0 by the addition of 5 NHCl, and the resulting solution was extracted 3 times with 1/2 volumes of $CH_2Cl_2$. The $CH_2Cl_2$ extracts were combined and evaporated under vacuum to give an oily residue. This residue was taken up in 500 ml of upper phase of the solvent system hexane:methanol:water (10:7:1). The upper phase was extracted 6 times with 300-ml portions of lower phase. These extracts were combined and concentrated under vacuum to give a residue. This residue was dissolved in dioxane; the dioxane solution was lyophilized to give 19.4 g of deoxynarasin complex.

Several samples, obtained in the same manner, were combined (40 g), dissolved in toluene and loaded onto a silica-gel column in a liquid chromatograph (Waters' Associates Prep. LC/System 500). The column was eluted with a toluene: ethyl acetate (9:1) solvent system at a flow rate of 250 ml/min, collecting fractions having a volume of 250 ml. Fraction content was monitored by TLC. Fractions 37–52 were combined and concentrated under vacuum to give a residue which was redissolved in dioxane and lyophilized to give 7.8 g of purified material rich in 20-deoxynarasin. This material was rechromatographed on the Water's Prep. LC/System 500 as above described. After eluting 50 fractions with the toluene:ethyl acetate (9:1) solvent system, the eluting solvent was changed to 100% ethyl acetate. Fractions 51–53 were combined and evaporated under vacuum to give a residue which was dissolved in dioxane and lyophilized to give 1.12 g of 20-deoxynarasin as its sodium salt.

EXAMPLE 5

Preparation of 20-Deoxynarasin Free Acid

20-Deoxynarasin sodium salt (200 mg) was dissolved in ethyl acetate (10 ml). This solution was washed with 0.1 N HCl (10 ml) and then twice with water (5 ml). The resulting organic layer was evaporated to dryness to give a residue which was redissolved in dioxane and lyophilized to give 139.6 mg of 20-deoxynarasin free acid as a white solid.

EXAMPLE 6

Chick Ration for Coccidiosis Control

A balanced, high-energy ration adapted to feed chicks for rapid weight gain is prepared by the following recipe:

| Ingredient | % | lbs |
|---|---|---|
| Ground yellow corn | | 1,000 |
| Soybean meal, solvent-extracted dehulled, finely ground, 50 percent protein | 30.9 | 618 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phospate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Salt (NaCl) | 0.3 | 6 |
| Trace mineral premix (representing $MnSO_4$, ZnO, KI, $FeSO_4$, $CaCO_3$) | 0.1 | 2 |
| 2-Amino-4-hydroxybutyric acid (hydroxy analog of methionine) | 0.1 | 2 |

Deoxynarasin antibiotic complex, 20-deoxynarasin or 20-deoxy-epi-17-narasin (about 0.01% by weight) is mixed with this ration in accordance with standard feedmixing techniques. Chicks fed such a ration, with water ad libitum, are protected against exposure to coccidiosis.

EXAMPLE 7

Improved Beef-Cattle Ration

A balanced high-grain beef-cattle ration is prepared as follows:

| Ingredient | % | lbs |
|---|---|---|
| Finely ground corn | 67.8 | 1,356 |
| Ground corn cob | 10 | 200 |
| Dehydrated alfalfa meal, 17 percent protein | 5 | 100 |
| Dehulled soybean meal, solvent extracted, 50 percent protein | 10 | 200 |
| Cane molasses | 5 | 100.0 |

-continued

| Ingredient | % | lbs |
|---|---|---|
| Urea | 0.6 | 12.0 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and D$_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin D$_2$ and 385.7 g of soybean feed with 1% oil added
**Corn distillers dried grains with solubles containing 20,000 I.U. of d-alpha-tocopheryl acetate per pound Deoxynarasin antibiotic complex, 20-deoxynarasin or 20-deoxy-epi-17-narasin (about 0.004% by weight) is mixed with this ration according to standard techniques. The mixed feed is compressed into pellets. At an average daily ingestion rate of 15 pounds of feed per animal, this feed supplies approximatey 300 mg of antiobiotic per animal per day.

EXAMPLE 8

Improved Swine Ration

A premix is prepared by standard methods using the following ingredients:

| Ingredient | Grams/Kilogram |
|---|---|
| Active Compound | 150.0 |
| Calcium Silicate | 20.0 |
| Calcium Carbonate (Oyster Shell Flour) | 830.0 |
| Total Weight | 1000 gms. |

This premix is added to commercial swine ration, using standard feed-mixing techniques to give a final level of active compound of 100 grams/ton.

We claim:

1. The method of producing the deoxynarasin antibiotic complex which comprises cultivating *Streptomyces aureofaciens* NRRL 11181 or a deoxynarasin-producing mutant thereof in a culture medium containing assimilable sources of carbohydrate, nitrogen, and inorganic salts under submerged aerobic fermentation conditions until a substantial amount of antiobiotic activity is produced.

2. The method of claim 1 wherein the *Streptomyces aureofaciens* is NRRL 11181.

3. The method of claim 1 which includes the additional step of isolating the deoxynarasin antibiotic complex from the culture medium.

4. The method of claim 3 which includes the additional step of isolating 20-deoxynarasin from the separated deoxynarasin complex.

5. The method of claim 3 which includes the additional step of isolating 20-deoxy-epi-17-narasin from the separated deoxynarasin complex.

* * * * *